United States Patent
Lu et al.

(10) Patent No.: US 10,954,555 B2
(45) Date of Patent: Mar. 23, 2021

(54) ANTHRANILATE SYNTHASE ALLELE FRAGMENTS FOR INCREASING RICE YIELD AND USES THEREOF

(71) Applicant: Institute of Botany, The Chinese Academy of Sciences, Beijing (CN)

(72) Inventors: Yingqing Lu, Beijing (CN); Nan Li, Beijing (CN); Lulu Xie, Beijing (CN); Yiting Wang, Beijing (CN); Ruijuan Zhang, Beijing (CN); Jingdan Chen, Beijing (CN)

(73) Assignee: Institute of Botany, The Chinese Academy of Scienc, Beijing (CN)

( * ) Notice: Subject to any disclaimer, the term of this patent is extended or adjusted under 35 U.S.C. 154(b) by 0 days.

(21) Appl. No.: 16/299,290

(22) Filed: Mar. 12, 2019

(65) Prior Publication Data

US 2019/0367973 A1 Dec. 5, 2019

(30) Foreign Application Priority Data

Mar. 16, 2018 (CN) .......................... 20181021682.X

(51) Int. Cl.
 *C12Q 1/6895* (2018.01)
 *C12Q 1/6858* (2018.01)
 *A01H 1/04* (2006.01)

(52) U.S. Cl.
 CPC ......... *C12Q 1/6858* (2013.01); *C12Q 1/6895* (2013.01); *A01H 1/04* (2013.01)

(58) Field of Classification Search
 None
 See application file for complete search history.

(56) References Cited

PUBLICATIONS

Tozawa et al. Plant Physiology (2001) 126:1493-1506.*

* cited by examiner

*Primary Examiner* — Medina A Ibrahim

(57) ABSTRACT

Anthranilate synthase allele fragments for increasing rice yields and uses thereof. A method of differentiating rice materials with a superior allele associated with high yield includes: (1) detecting a genotype of rice to be detected based on a specific gene fragment; where the specific gene fragmentOsASA1 is located in rice genome, and there are typically two allelic forms of OsASA1, OsASA1_a shown as SEQ ID NO. 1 and OsASA1_b shown as SEQ ID NO. 2; and (2) determining and comparing the average yield of a rice population with a genotype of homozygous OsASA1_b and that of a rice population with a genotype of homozygous OsASA1_a under the same growth conditions in different geographical regions. The rice population with the genotype of homozygous OsASA1_b shows a higher average yield than the rice population with the genotype of homozygous OsASA1_a.

5 Claims, No Drawings

Specification includes a Sequence Listing.

ANTHRANILATE SYNTHASE ALLELE FRAGMENTS FOR INCREASING RICE YIELD AND USES THEREOF

REFERENCE TO AN ELECTRONIC SEQUENCE LISTING

The contents of the electronic sequence listing (Untitled_ST25.txt; Size: 4,000 bytes; and Date of Creation: Aug. 17, 2019) is herein incorporated by reference in its entirety.

CROSS-REFERENCE TO RELATED APPLICATIONS

This application claims the benefit of priority from Chinese Patent Application No. 201810217682.X, filed on Mar. 16, 2018. The content of the aforementioned application, including any intervening amendments thereto, is incorporated herein by reference in its entirety.

TECHNICAL FIELD

The present application relates to biotechnology, and particularly to an allele fragment and specific primer pair for cultivating universal high-yield rice, and more particularly to an anthranilate synthase allele fragment for increasing rice yields and a use thereof.

BACKGROUND

Rice (*Oryza sativa* L.) is consumed as a staple food for more than half of the world's population. There is an increasing need to cultivate high-yield rice varieties with the growth of population. Knowing genomic components of rice for determining the traits contributing to high yield is critical for the targeted selection of parental materials in the breeding process and cultivation of rice varieties with high-yield traits.

In practice, the basic goal of rice breeding is to introduce good traits into the same variety, so that it can provide high-yield and good-quality rice in a wide range of geographical conditions. Currently, most breeding methods rely on observable traits or/and molecular markers. While factors affecting rice traits are often diverse and complex, methods to improve such traits rely on the evaluation of single or multiple reported genes. Little is known of particular allelic effects of genome on desired traits.

The significance of gene functional analysis to agricultural breeding lies in whether or not the research is conducted under the field condition to be relevant to the typical rice-growing practice. Typical studies of natural variation in rice populations have focused on single nucleotide polymorphisms, and studies using genome-wide association have identified some correlations between phenotypes and single nucleotide polymorphisms. However, effects of the studies on agricultural breeding remain to be assessed.

The development of molecular biology in recent decades has given rise to molecular breeding. Breeding with specific genes or molecular markers as selectors has improved the success rate of traditional breeding. In terms of yield, one of the constraints of molecular breeding is determining which genes or molecular fragments are most suitable as selectors.

SUMMARY

The present application provides an allele and a specific primer pair for cultivating high-yield rice and a method for screening rice materials of potential high-yield traits.

In an embodiment, a method of screening high-yield rice under different geographical conditions comprises:

(1) detecting a genotype of rice to be detected based on a specific gene fragment; wherein the specific gene fragmentOsASA1 is located in rice genome, and there are typically two allelic forms of OsASA1, OsASA1_a shown as SEQ ID NO. 1 and OsASA1_b shown as SEQ ID NO. 2; and (2) determining and comparing the average yield of a rice population with a genotype of homozygous OsASA1_b and that of a rice population with a genotype of homozygous OsASA1_a under the same growth conditions in different geographical regions; wherein the rice population with the genotype of homozygous OsASA1_b shows a higher average yield than the rice population with the genotype of homozygous OsASA1_a across regions; OsASA1_b is the superior allele for rice yield.

The same growth conditions in different geographical regions means that the growth conditions are the same but the geographical regions are different.

In an embodiment, a method of screening high-yield rice under different geographical conditions comprises:

(1) amplifying genomic DNA of rice to be detected with a specific primer pair by PCR; wherein if there is only one type of PCR amplification product shown as SEQ ID NO. 1, a genotype of the rice to be detected is homozygousOsASA1_a, and if there is only one type of PCR amplification product shown as SEQ ID NO. 2, a genotype of the rice to be detected is homozygousOsASA1_b; and (2) determining and comparing the average yield of a rice population with a genotype of homozygous OsASA1_b and that of a rice population with a genotype of homozygous OsASA1_a under the same growth conditions in different geographical regions; wherein the rice population with the genotype of homozygous OsASA1_b shows a higher average yield than the rice population with the genotype of homozygous OsASA1_a across regions; OsASA1_b is the superior allele for rice yield.

In an embodiment, a method of screening high-yield rice comprises:

(1) detecting a genotype of rice to be detected based on a specific gene fragment; wherein the specific gene fragment, OsASA1, is located in rice genome, and there are two allelic forms of OsASA1, OsASA1_a shown as SEQ ID NO. 1 and OsASA1_b shown as SEQ ID NO. 2; and (2) determining and comparing the average yield of a rice population with a genotype of homozygous OsASA1_b and that of a rice population with a genotype of homozygous OsASA1_a under the same growth conditions in different geographical regions; wherein the rice population with the genotype of homozygous OsASA1_b shows a higher average yield than the rice population with the genotype of homozygous OsASA1_a across regions; OsASA1_b is the superior allele for rice yield.

In an embodiment, a method of screening high-yield rice comprises:

(1) amplifying genomic DNA of rice to be detected with a specific primer pair by PCR where if there is only one type of PCR amplification product shown as SEQ ID NO. 1, a genotype of the rice to be detected is homozygousOsASA1_a; and if there is only one type of PCR amplification product shown as SEQ ID NO. 2, a genotype of the rice to be detected is homozygousOsASA1_b; and (2) determining and comparing the average yield of a rice population with a genotype of homozygous OsASA1_b and that of a rice population with a genotype of homozygous OsASA1_a under the same growth conditions in different geographical regions; wherein the rice population with the genotype of homozygous OsASA1_b shows a higher average yield than the rice population with the genotype of homozygous OsASA1_a across regions; OsASA1_b is the superior allele for rice yield.

The same growth conditions may be in the same geographical regions.

The growth conditions consist of natural environment (including soil temperature, humidity and nutrient, etc.) and labor management (including fertilization, pesticide application and bird repelling, etc.).

In an embodiment, a method of screening high-yield rice comprises: (1) detecting a genotype of rice to be detected based on a specific gene fragment; wherein the specific gene fragmentOsASA1 is located in rice genome, and there are typically two allelic forms of OsASA1, OsASA1_a shown as SEQ ID NO. 1 and OsASA1_b shown as SEQ ID NO. 2; and (2) selecting rice with a genotype of homozygous OsASA1_b as the rice of interest.

In an embodiment, a method of screening high-yield rice comprises:

(1) amplifying genomic DNA of rice to be detected with the a specific primer pair by PCR; where if there is only one type of PCR amplification product shown as SEQ ID NO. 1, a genotype of the rice to be detected is homozygousOsASA1_a; and if there is only one type of PCR amplification product shown as SEQ ID NO. 2, a genotype of the rice to be detected is homozygousOsASA1_b; and (2) selecting rice with a genotype of homozygous OsASA1_b as the rice of interest.

The rice of interest is high-yield rice.

In an embodiment, the specific primer pair as described above consists of a first primer and a second primer.

The first primer may be selected from:

(a1) a single-stranded DNA molecule shown as SEQ ID NO. 3; or (a2) a single-stranded DNA molecule derived from SEQ ID NO. 3 through substitution and/or deletion and/or addition of one or more nucleotides and having the same function as SEQ ID NO. 3.

The second primer may be selected from:

(b1) a single-stranded DNA molecule shown as SEQ ID NO. 4; or (b2) a single-stranded DNA molecule derived from SEQ ID NO. 4 through substitution and/or deletion and/or addition of one or more nucleotides and having the same function as SEQ ID NO. 4.

The application further provides a specific allelic fragment, which may be OsASA1_a or OsASA1_b.

OsASA1_a is selected from:

(c1) a DNA molecule shown as SEQ ID NO. 1; or (c2) a DNA molecule derived from SEQ ID NO. 1 through substitution and/or deletion and/or addition of one or more nucleotides and having the same function as SEQ ID NO. 1.

OsASA1 b is selected from:

(d1) a DNA molecule shown as SEQ ID NO. 2; or (d2) a DNA molecule derived from SEQ ID NO. 2 through substitution and/or deletion and/or addition of one or more nucleotides and having the same function as SEQ ID NO. 2.

In (c2) or (d2), the "substitution and/or deletion and/or addition" occurs at the regions other than three differences between SEQ ID NO. 1 and SEQ ID NO. 2.

The application further provides a kit comprising the specific primer pair. In an embodiment, the kit further comprises a conventional reagent for extracting genomic DNA from rice and/or a conventional reagent for PCR amplification and/or a conventional reagent for sequencing.

In an embodiment, a use method of the kit comprises:
applying the kit to any of the following:
(e1) screening for high-yield rice under different geographical conditions;
(e2) screening for rice with different yield traits;
(e3) identification of yield traits of rice; and
(e4) identification of rice with different yield traits;

In an embodiment, the application further provides a method for preparing the kit, comprising:
separately packaging each of the primers in the kit.

In an embodiment, a use method of the specific allelic fragment or the specific primer pair comprises:
(e1) screening for high-yield rice under different geographical conditions;
(e2) screening for rice with different yield traits;
(e3) identification of yield traits of rice; and
(e4) identification of rice with different yield traits:

The specific allelic fragment, the specific primer pair, the kit and use methods thereof in rice breeding are also within the scope of the invention. The goal of the rice breeding is to obtain high-yield rice.

Any of the yield described herein may be a single plant yield or a grain yield.

In an embodiment, the invention further provides a method for identifying a superior allele, comprising: determining an allele with a superior trait by comparison of differences in biological traits among different populations; where each population consists of homozygous individuals with regard to the allele and other alleles of the same gene.

Organism may be of sexual reproduction; particularly, a plant; and more particularly, rice.

The trait may be a measurable trait; particularly, a yield trait; and more particularly, a grain yield trait.

The experiments demonstrate that the method of the invention can be used to screen rice with different yield traits, and involves simple process and high accuracy, thereby playing an important role in rice breeding.

DETAILED DESCRIPTION OF EMBODIMENTS

Unless otherwise specified, the experimental methods used in the following examples are conventional methods.

Unless otherwise specified, materials and reagents used in the following examples are commercially available.

The invention will be further described in detail with reference to the embodiments. These embodiments are merely for illustration, but are not intended to limit the scope of the invention.

Example 1 Design and Synthesis of Primers

Anthranilic acid is an important precursor for the synthesis of tryptophan and guanidine in rice. In the rice genome, at least one gene has been annotated to encode anthranilate synthase (EC 4.1.3.27), called anthranilate synthase alpha 1 (AB022602.1; OsASA1) gene (referred to as OsASA1 gene thereafter). The OsASA1 gene is located on chromosome 3 of rice. Based on a large number of pre-experiments and sequence alignments, it has been found that there were at least two allelic fragments in the OsASA1 gene, OsASA1_a shown as SEQ ID NO. 1 and OsASA1_b shown as SEQ ID NO.2. These allelic fragments were associated with yield per plant of rice.

A specific primer pair consisting of a first primer and a second primer was designed based on the two kinds of allelic fragments.

```
First primer (shown as SEQ ID NO. 3):
5'-GTTACTGGAGAGTTGCGTGATG-3'.

Second primer (shown as SEQ ID NO. 4):
5'-CTCATCTACGAATGTAGACTCGGC-3'.
```

Example 2 Establishment of Typing Method Based on the Allelic Fragments in Rice

The method was described as follows.

1. The specific primer pair consisting of the first primer and the second primer was used to amplify genomic DNA (about 10-100 ng) of rice to be detected by PCR to obtain a PCR amplification product. The PCR amplification was programmed as follows: 35 cycles, for each cycle, 95° C. for 5 minutes, 95° C. for 30 seconds, 61° C. for 1 minute and 72° C. for 1 minute; and then 72° C. for 8 minutes before cooling.

2. The PCR amplification product was sequenced, and the results were determined as follows. If there was only one type of the PCR amplification product shown as SEQ ID NO. 1, the genotype of the rice was homozygous OsASA1_a; and if there was only one type of the PCR amplification product shown as SEQ ID NO. 2, the genotype of the rice to be detected was homozygous OsASA1_b; and if there were two types of the PCR amplification product respectively shown as SEQ ID NO. 1 and SEQ ID NO. 2, the genotype of the rice was heterozygous OsASA1_a/OsASA1_b.

Due to monoculture of cultivars or landraces and selfing, the proportion of homozygous individuals is typically high.

Example 3 Correlation Analysis Between Genotype of Rice Based on the Allelic Fragment and Yield Per Plant 1. Statistics on yield per plant of different rice varieties Numerous rice varieties were planted in Sanya (Hainan) and Beijing in 2014 (see Tables 1-2 for details, where the rice variety names were shown in columns 2; the origins of rice varieties were shown in columns 3; and the 2009 numbers of some rice varieties (according to Biotechnology and Germplasm Resources Institute. Academy of Agricultural Sciences, Yunnan) were shown in column 6. A completely random trial was designed in the field. The mature rice plants were harvested by individual plants, weighed and averaged to obtain the yield per plant (see columns 5 in Tables 1 and 2).

2. Genotypes of each rice variety were detected according to the typing method in Example 2 (see columns 4 in Tables 1 and 2).

TABLE 1

Experiments in Sanya

| Number | Variety | Origin | Genotype | Yield per plant (g) | 2009 Number |
|---|---|---|---|---|---|
| 1 | Kendao 12 | Kiamusze, Heilongjiang | OsASA1_a | 19.6 | |
| 2 | Kendao 16 | Kiamusze, Heilongjiang | OsASA1_a | 29.2 | |
| 3 | Kendao 25 | Kiamusze, Heilongjiang | OsASA1_a | 37.5 | |
| 4 | Kendao 9 | Kiamusze, Heilongjiang | OsASA1_a | 21.8 | |
| 5 | Kenjiandao 3 | Kiamusze, Heilongjiang | OsASA1_a | 42.4 | |
| 6 | Kenjiandao 6 | Kiamusze, Heilongjiang | OsASA1_a | 23.2 | |
| 7 | Kongyu 131 | Kiamusze, Heilongjiang | OsASA1_a | 41.6 | |
| 8 | Longhua 04426 | Kiamusze, Heilongjiang | OsASA1_a | 31.7 | |
| 9 | Longjiao 04-2411 | Kiamusze, Heilongjiang | OsASA1_a | 41.9 | |
| 10 | Longjing 26 | Kiamusze, Heilongjiang | OsASA1_a | 16.4 | |
| 11 | Longjing 27 | Kiamusze, Heilongjiang | OsASA1_a | 57.2 | |
| 12 | Longjing 29 | Kiamusze, Heilongjiang | OsASA1_a | 32.2 | |
| 13 | Longjingxiang 1 | Kiamusze, Heilongjiang | OsASA1_a | 26.1 | |
| 14 | Longsheng 04042 | Kiamusze, Heilongjiang | OsASA1_a | 22.4 | |
| 15 | Songjing 10 | Wuchang, Heilongjiang | OsASA1_a | 16.3 | |
| 16 | Songjing 11 | Wuchang, Heilongjiang | OsASA1_a | 49.3 | |
| 17 | Songjing 13 | Wuchang, Heilongjiang | OsASA1_a | 48.6 | |
| 18 | Songjing 15 | Wuchang, Heilongjiang | OsASA1_a | 40.6 | |
| 19 | Songjing 16 | Wuchang, Heilongjiang | OsASA1_a | 19.6 | |
| 20 | Songjing 17 | Wuchang, Heilongjiang | OsASA1_a | 32.1 | |
| 21 | Songjing 18 | Wuchang, Heilongjiang | OsASA1_a | 33.3 | |
| 22 | Songzhan 1 | Wuchang, Heilongjiang | OsASA1_a | 38.0 | |
| 23 | Suijing 10 | Suihua, Heilongjiang | OsASA1_a | 22.5 | |
| 24 | Suijing 4 | Suihua, Heilongjiang | OsASA1_a | 28.2 | |
| 25 | Longjin 1 | Gongzhuling, Jilin | OsASA1_a | 12.0 | |
| 26 | Liaoxing 20 | Shenyang, Liaoning | OsASA1_a | 35.6 | |
| 27 | Fengdao 21 | Dali, Yunnan | OsASA1_a | 22.5 | |
| 28 | Xiujing 20 | Baoshan, Yunnan | OsASA1_a | 36.6 | |
| 29 | Yunjing 29 | Nanhua Agricultural technical station seed station, Chuxiong, Yunnan | OsASA1_a | 48.1 | |
| 30 | Haomuhao | Biotechnology and Germplasm Resources Institute, Academy of Agricultural Sciences, Yunnan | OsASA1_a | 48.0 | 1551 |
| 31 | Jieba | Biotechnology and Germplasm Resources Institute, Academy of Agricultural Sciences, Yunnan | OsASA1_a | 23.1 | 1065 |

TABLE 1-continued

| | | Experiments in Sanya | | | |
|---|---|---|---|---|---|
| Number | Variety | Origin | Genotype | Yield per plant (g) | 2009 Number |
| 32 | Mengxinggu | Biotechnology and Germplasm Resources Institute, Academy of Agricultural Sciences, Yunnan | OsASA1_a | 62.0 | 1640 |
| 33 | Songjing 12 | Wuchang, Heilongjiang | OsASA1_b | 25.5 | |
| 34 | Songjing 19 | Wuchang, Heilongjiang | OsASA1_b | 22.2 | |
| 35 | Manglongxichanggu | Biotechnology and Germplasm Resources Institute, Academy of Agricultural Sciences, Yunnan | OsASA1_b | 75.0 | 1196 |
| 36 | Xiaoxigu | Biotechnology and Germplasm Resources Institute, Academy of Agricultural Sciences, Yunnan | OsASA1_b | 77.2 | 1651 |
| 37 | Nuogu | Biotechnology and Germplasm Resources Institute, Academy of Agricultural Sciences, Yunnan | OsASA1_b | 43.2 | 1144 |
| 38 | Changruanmi | Biotechnology and Germplasm Resources Institute, Academy of Agricultural Sciences, Yunnan | OsASA1_b | 44.5 | 1140 |
| 39 | Tianza | Biotechnology and Germplasm Resources Institute, Academy of Agricultural Sciences, Yunnan | OsASA1_b | 51.9 | 1282 |
| 40 | Mengsonggu | Biotechnology and Germplasm Resources Institute, Academy of Agricultural Sciences, Yunnan | OsASA1_b | 49.4 | 1012 |
| 41 | Changbainuo | Biotechnology and Germplasm Resources Institute, Academy of Agricultural Sciences, Yunnan | OsASA1_b | 39.8 | 1364 |
| 42 | Dahonggu | Biotechnology and Germplasm Resources Institute, Academy of Agricultural Sciences, Yunnan | OsASA1_b | 48.8 | 1436 |
| 43 | Menglagu | Biotechnology and Germplasm Resources Institute, Academy of Agricultural Sciences, Yunnan | OsASA1_b | 40.6 | 1643 |
| 44 | Yunhui 290 | Biotechnology and Germplasm Resources Institute, Academy of Agricultural Sciences, Yunnan | OsASA1_b | 25.3 | 1638 |
| 45 | Xiangsigu | Biotechnology and Germplasm Resources Institute, Academy of Agricultural Sciences, Yunnan | OsASA1_b | 41.2 | 1017 |
| 46 | Shuijinghangu | Biotechnology and Germplasm Resources Institute, Academy of Agricultural Sciences, Yunnan | OsASA1_b | 23.4 | 1120 |
| 47 | Xiaohuanggu | Biotechnology and Germplasm Resources Institute, Academy of Agricultural Sciences, Yunnan | OsASA1_b | 30.9 | 1655 |
| 48 | Yidunban | Biotechnology and Germplasm Resources Institute, Academy of Agricultural Sciences, Yunnan | OsASA1_b | 63.8 | 1032 |
| 49 | Mengpenggu | Biotechnology and Germplasm Resources Institute, Academy of Agricultural Sciences, Yunnan | OsASA1_b | 94.0 | 1068 |
| 50 | Ruiligu | Biotechnology and Germplasm Resources Institute, Academy of Agricultural Sciences, Yunnan | OsASA1_b | 39.4 | 1192 |
| 51 | Honggu | Biotechnology and Germplasm Resources Institute, Academy of Agricultural Sciences, Yunnan | OsASA1_b | 50.4 | 1381 |
| 52 | Haonuolong | Biotechnology and Germplasm Resources Institute, Academy of Agricultural Sciences, Yunnan | OsASA1_b | 34.9 | 1043 |
| 53 | Hongxinmo | Biotechnology and Germplasm Resources Institute, Academy of Agricultural Sciences, Yunnan | OsASA1_b | 25.9 | 1652 |

The results in Table 1 indicated that 32 varieties among the 53 random rice varieties had the genotype of homozygous OsASA1_a, and the average yield per plant for these 32 varieties was 33.11±2.21 g. The rest of 21 varieties among the 53 random rice varieties, with die genotype of homozygous OsASA1_b, exhibited an average yield per plant of 45.11±4.17 g. The average yield per plant of the varieties with a genotype of homozygous OsASA1_a was significantly different from that of those with a genotype of homozygous OsASA1_b by two-tailed t-test, (P, 0.016).

TABLE 2

Experiments in Beijing

| Number | Variety | Origin | Genotype | Yield per plant (g) |
|---|---|---|---|---|
| 1 | Zhonghua 15 | Beijing | OsASA1_a | 44.54 |
| 2 | Kendao 12 | Kiamusze, Heilongjiang | OsASA1_a | 14.45 |
| 3 | Kendao 16 | Kiamusze, Heilongjiang | OsASA1_a | 17.57 |
| 4 | Kenjiandao 3 | Kiamusze, Heilongjiang | OsASA1_a | 15.41 |
| 5 | Kenjiandao 6 | Kiamusze, Heilongjiang | OsASA1_a | 29.08 |
| 6 | Longjiao 04-1963 | Kiamusze, Heilongjiang | OsASA1_a | 13.79 |
| 7 | Longjing 39 | Kiamusze, Heilongjiang | OsASA1_a | 23.67 |
| 8 | Longjing 40 | Kiamusze, Heilongjiang | OsASA1_a | 12.10 |
| 9 | Longjing 41 | Kiamusze, Heilongjiang | OsASA1_a | 17.61 |
| 10 | Longjingxiang 1 | Kiamusze, Heilongjiang | OsASA1_a | 20.81 |
| 11 | Longsheng 04042 | Kiamusze, Heilongjiang | OsASA1_a | 13.94 |
| 12 | Songjing 16 | Wuchang, Heilongjiang | OsASA1_a | 15.92 |
| 13 | Songjing 18 | Wuchang, Heilongjiang | OsASA1_a | 30.50 |
| 14 | Songzhan 1 | Wuchang, Heilongjiang | OsASA1_a | 16.49 |
| 15 | Suijing 10 | Suihua, Heilongjiang | OsASA1_a | 11.63 |
| 16 | Suijing 4 | Suihua, Heilongjiang | OsASA1_a | 18.48 |
| 17 | Suijing 8 | Suihua, Heilongjiang | OsASA1_a | 13.34 |
| 18 | Jijing 810 | Jilin | OsASA1_a | 8.62 |
| 19 | Jizhan 9 | Jilin | OsASA1_a | 32.36 |
| 20 | Longjin 1 | Gongzhuling, Jilin | OsASA1_a | 40.71 |
| 21 | Changbai 22 | Changbai Mountain, Jilin | OsASA1_a | 22.82 |
| 22 | 9600 | Jiangsu | OsASA1_a | 48.44 |
| 23 | 9924 | Jiangsu | OsASA1_a | 22.15 |
| 24 | Huajing 6 | Jiangsu | OsASA1_a | 13.19 |
| 25 | Wuyujing 3 | Jiangsu | OsASA1_a | 12.34 |
| 26 | Zaohua 75 | Jiangsu | OsASA1_a | 28.80 |
| 27 | Zhen 88 | Jiangsu | OsASA1_a | 30.10 |
| 28 | Dongshi 15 | Liaoning | OsASA1_a | 61.09 |
| 29 | Liaojing 287 | Liaoning | OsASA1_a | 25.83 |
| 30 | Liaoxing 15 | Liaoning | OsASA1_a | 17.74 |
| 31 | Liaoxing 20 | Liaoning | OsASA1_a | 30.69 |
| 32 | Liaoxing 9 | Liaoning | OsASA1_a | 41.94 |
| 33 | Shennong 47 | Liaoning | OsASA1_a | 42.93 |
| 34 | Shennong 9 | Liaoning | OsASA1_a | 66.49 |
| 35 | Yanfeng 47-38 | Liaoning | OsASA1_a | 21.98 |
| 36 | Yanjing 200 | Liaoning | OsASA1_a | 26.25 |
| 37 | Yanjing 456 | Liaoning | OsASA1_a | 26.28 |
| 38 | Sheng 102 | Shandong | OsASA1_a | 18.85 |
| 39 | Aituogu 151 | Sichuan | OsASA1_a | 53.79 |
| 40 | Xindao 27 | Yili, Xinjiang | OsASA1_a | 39.37 |
| 41 | Fengdao 21 | Dali, Yunnan | OsASA1_a | 26.66 |
| 42 | Xiujing 20 | Baoshan, Yunnan | OsASA1_a | 13.76 |
| 43 | Yunjing 29 | Nanhua agricultural technical station-Seed station, Chuxiong, Yunnan | OsASA1_a | 19.48 |
| 44 | Guangzhan 63 | Guangdong | OsASA1_b | 12.30 |
| 45 | Guiyaug 2 | Guangdong | OsASA1_b | 18.99 |
| 46 | Wanxian 98 | Guangdong | OsASA1_b | 39.64 |
| 47 | Zhaoyeqing | Guangdong | OsASA1_b | 71.18 |
| 48 | Huanglizhanguang 3 | Guangdong | OsASA1_b | 28.30 |
| 49 | Huanghuazhanguang 4 | Guangdong | OsASA1_b | 57.22 |
| 50 | Guichao 2 | Guangdong | OsASA1_b | 21.74 |
| 51 | Huangsiguizhan | Guangdong | OsASA1_b | 38.78 |
| 52 | Songjing 3 | Wuchang, Heilongjiong | OsASA1_b | 12.31 |
| 53 | Songjing 13 | Wuchang, Heilongjiong | OsASA1_b | 20.97 |
| 54 | Xiangaizao 10 | Human | OsASA1_b | 31.34 |
| 55 | Jinong 316 | Jilin | OsASA1_b | 21.89 |
| 56 | Changbai 9 | Changbaishan, Jilin | OsASA1_b | 31.85 |
| 57 | Jijing 105 | Jilin | OsASA1_b | 35.36 |
| 58 | Jijing 803 | Jilin | OsASA1_b | 45.20 |
| 59 | Wuyunjing 21 | Jiangsu | OsASA1_b | 14.72 |
| 60 | 9311 | Jiangsu | OsASA1_b | 55.15 |
| 61 | Zhenxian 96 | Jiangsu | OsASA1_b | 55.90 |
| 62 | Shuchang 251 | Liaoning | OsASA1_b | 13.58 |
| 63 | Zhonghua 58 | Liaoning | OsASA1_b | 25.53 |
| 64 | Luke 3号 | Sichuan | OsASA1_b | 28.31 |
| 65 | Shufeng 101 | Sichuan | OsASA1_b | 51.17 |
| 66 | Shufeng 101 | Sichuan | OsASA1_b | 51.17 |

The results in Table 2 showed that 44 varieties among the 66 random rice varieties had the genotype of homozygous OsASA1_a, and the average yield per plant for these 44 varieties was 25.78 12.09 g. The rest of 22 varieties among the 66 random rice varieties, with the genotype of homozygous OsASA1_b, exhibited an average yield per plant of 33.25:3.57 g. The average yield per plant of the varieties with a genotype of homozygous OsASA1_a was significantly different from that with a genotype of homozygous OsASA1_b by two-tailed t-test (P, 0.015).

3. Development of method for screening rice with different yield traits per plant The method was described as follows.

(1) The genotype of rice to be detected was detected based on a specific gene fragment, where the specific gene fragment, OsASA1, was located in rice genome, and there were at least two allelic forms of OsASA1. OsASA1_a shown as SEQ ID NO. 1 and OsASA1_b shown as SEQ ID NO. 2.

(2) The average yield of a rice population with a genotype of homozygous OsASA1_b and that of a rice population with a genotype of homozygous OsASA1_a were determined and compared under the same growth conditions in different geographical regions. The results indicated that the rice population with the genotype of homozygous OsASA1_b showed a higher average yield per plant than the rice population with the genotype of homozygous OsASA1_a.

What is claimed is:

1. A method for breeding rice plants having increased yield, comprising:
   detecting a genotype of OsASA1 gene in rice plants;
   selecting a rice plant with a homozygous genotype of OsASA1_b allele; and
   crossing the selected rice plant with a second rice plant lacking the homozygous genotype of OsASA1_b allele to produce progeny rice plants having increased yield;
   wherein the nucleotide sequence of the OsASA1_b allele is shown as SEQ ID NO: 2.

2. The method of claim 1, wherein the step of detecting a genotype of OsASA1 gene in rice plants comprises:
   screening genomes of the rice plants and determining a pair of alleles being OsASA1_a and OsASA1_b;
   comparing a first yield of the rice plants that carry a homozygous genotype of OsASA1_a allele, with a second yield of the rice plants that carry a homozygous genotype of OsASA1_b allele;
   based on a compared result that the second yield is higher than the first yield, pre-determining a target homozygous genotype as the OsASA1_b allele; and
   testing a third yield of rice plants with the OsASA1_b allele under various environments to confirm the rice plants having increased yield;
   wherein the nucleotide sequence of the OsASA1_a allele is shown as SEQ ID NO: 1.

3. The method of claim 2, wherein the genes of the rice plants are screened by PCR.

4. The method of claim 3, wherein a primer pair for the PCR comprises a first primer shown as SEQ ID NO: 3, and a second primer shown as SEQ ID NO: 4.

5. The method of claim 2, wherein the step of testing a third yield of rice plants with the OsASA1_b allele under various environments to confirm the rice plants having increased yield comprises:
   cultivating the rice plants with the OsASA1_b allele and rice plants with the OsASA1_a allele simultaneously under various environments; and
   in response to a determination that the third yield of the rice plants with the OsASA1_b allele is higher than a yield of the rice plants with the OsASA1_a allele, confirming the rice plants having increased yield.

* * * * *

SEQUENCE LISTING

```
<160> NUMBER OF SEQ ID NOS: 4

<210> SEQ ID NO 1
<211> LENGTH: 796
<212> TYPE: DNA
<213> ORGANISM: Artificial Sequence
<220> FEATURE:
<223> OTHER INFORMATION: synthetic

<400> SEQUENCE: 1
gttactggag agttgcgtga tgatctgact tgttgggatg ctcttcgagc agcattgccc     60
gttggaacag ttagtggtgc accaaaggta aggaaataca tgttggcacc gtatggttgc    120
atcacctgaa tgctgtttca gaaagaaaac gagaaacact ctgccaactc aatatatcta    180
tatgcgccat catattcatc agatattgac atgactgttg accatagttt gttaaccact    240
gccttccctt cgtttcatct acttcctccg tttcaggtta taagactttta tagtattgca    300 cacattcata taaatattaa tgaatctaaa cacatatata tgtctagatt cactaacata    360
tatatggatg tagacaatgc tagaaagtct tataaactga aacggaggga gtaacatcta    420
ccatgcatta ttcatgttcc accgagctca atctctcatc ctcgtcttca accaggtgag    480
agcgatggag ctgattgacc agatggaagg gaagatgcgt gggccgtaca gtggtggctt    540 tggagggggtt tctttccgtg gagacatgga catcgcactt gctctccgta ccatcgtctt    600
ccccacggga tctcgcttcg acaccatgta ctcctacact gacaagaatg ctcgtcagga    660
gtgggtggct caccttcagg ctggagctgg gatcgtcgct gacagcaagc ctgacgatga    720
gcatcaggag tgcttgaaca aggctgctgg ccttgctcgt gccatcgatc ttgccgagtc    780
tacattcgta gatgag                                                    796

<210> SEQ ID NO 2
<211> LENGTH: 796
<212> TYPE: DNA
<213> ORGANISM: Artificial Sequence
<220> FEATURE:
<223> OTHER INFORMATION: synthetic

<400> SEQUENCE: 2
gttactggag agttgcgtga tgatctgact tgttgggatg ctcttcgagc agcattgccc     60
gttggaacag ttagtggtgc accaaaggta aggaaataca tgttggcacc gtatggttgc    120
atcacctgaa tgctgtttca gaaagaaaac gagaaacact ctgccaaccc aatatatcta    180
tatgcgccat catattcatc agatattgac atgactgttg accatagttt gttaaccact    240
gccttccctt cgtttcatct acttcctccg tttcaggtta taagacttta tagtattgca    300
cacattcata taaatattaa tgaatctaaa cacatatata tgcctagatt cactaacata    360
```

```
tatatggatg tagacaatgc tagaaagtct tataaactga aacggaggga gtaacatcta    420
ccatgcatta ttcatgttcc accgagctca atctctcatc ctcgtcttca accaggtgag    480
agcgatggag ctgattgacc agatggaagg gaagatgcgt gggccgtaca gtggtggctt    540
tggaggggtt tctttccgtg gagacatgga catcgcactt gctctccgta ccatcgtctt    600
ccccacggga tctcgcttcg acaccatgta ctcctacact gacaagaatg ctcgtcagga    660
gtgggtggct caccttcagg ctggagctgg gatcgtcgct gacagcaagc ctgacgatga    720
gcatcaggag tgcttgaaca aggctgctgg ccttgctcgt gccatcgatc ttgccgagtc    780
tacattcgta gatgag                                                    796

<210> SEQ ID NO 3
<211> LENGTH: 22
<212> TYPE: DNA
<213> ORGANISM: Artificial Sequence
<220> FEATURE:
<223> OTHER INFORMATION: synthetic

<400> SEQUENCE: 3
gttactggag agttgcgtga tg                                              22

<210> SEQ ID NO 4
<211> LENGTH: 24
<212> TYPE: DNA
<213> ORGANISM: Artificial Sequence
<220> FEATURE:
<223> OTHER INFORMATION: synthetic

<400> SEQUENCE: 4
ctcatctacg aatgtagact cggc                                            24
```